United States Patent [19]

Cheminal et al.

[11] Patent Number: 5,430,205
[45] Date of Patent: Jul. 4, 1995

[54] PROCESS FOR THE PURIFICATION OF 1,1,1,2-TETRAFLUOROETHANE

[75] Inventors: Bernard Cheminal, Brignais; André Lantz, Vernaison; Eric Lacroix, Lyons, all of France

[73] Assignee: Elf Atochem, S.A., Puteaux, France

[21] Appl. No.: 329,600

[22] Filed: Oct. 26, 1994

[30] Foreign Application Priority Data

Oct. 26, 1993 [FR] France ............... 93 12734

[51] Int. Cl.⁶ .............................. C07C 17/38
[52] U.S. Cl. .................................... 570/177
[58] Field of Search .......................... 570/177

[56] References Cited

U.S. PATENT DOCUMENTS 5,326,918 7/1994 Correia ................... 570/177

FOREIGN PATENT DOCUMENTS 0548742 6/1993 European Pat. Off. ........... 570/177
5000972 1/1993 Japan ............................... 570/177

*Primary Examiner*—Alan Siegel
*Attorney, Agent, or Firm*—Morgan & Finnegan

[57] ABSTRACT

In order to remove the olefinic impurities (in particular 1-chloro-2,2-difluoroethylene and polyfluoropropenes) present in crude 1,1,1,2-tetrafluoroethane (F134a), a gaseous mixture of crude F134a, hydrofluoric acid and oxygen or air is treated in the gas phase, in the presence of a fluorination catalyst, at a temperature between 200° and 350° C. and at a pressure between atmospheric pressure and 2.5 MPa, the HF/F134a molar ratio being between 0.05 and 0.5 and the $O_2$/F134a molar ratio being between 0.001 and 0.1.

10 Claims, No Drawings

PROCESS FOR THE PURIFICATION OF 1,1,1,2-TETRAFLUOROETHANE

FIELD OF THE INVENTION

The present invention relates to the field of fluorinated hydrocarbons and, more particularly, has as its subject the purification of 1,1,1,2-tetrafluoroethane.

BACKGROUND OF THE INVENTION

This compound, known in the profession under the name F134a, is especially intended to replace dichlorodifluoromethane (F12) currently used as a refrigerating fluid but suspected of contributing to the depletion of the stratospheric ozone layer. In order to do this, F134a must satisfy quality standards with respect to the presence of a priori toxic impurities, such as chlorofluorinated olefins.

Now, one of the industrial syntheses of F134a consists of a gas phase catalytic fluorination of trichloroethylene or of 1-chloro-2,2,2-trifluoroethane (F133a) which always produces, as a by-product, variable quantities of 1-chloro-2,2-difluoroethylene (F1122) which, given its boiling point ($-17.7°$ C.), proves to be very difficult to completely remove from F134a (B.p.$= -26.5°$ C.) by simple distillation, especially under pressure.

The F134a obtained according to this process or according to other processes generally further contains other olefinic compounds such as fluorinated propenes or butenes. The $C_4$ olefins such as $CF_3CF=CF-CF_3$ (F1318), $CF_3CF=CHCF_3$ (F1327), $CF_3CH=CClCF_3$ (F1326) and $CF_3=CHCF_3$ (F1336) are not particularly troublesome because they can be separated from F134a by distillation. F134a obtained industrially, in particular that obtained by gas phase fluorination of trichloroethylene or of F133a, generally contains more or less significant quantities of polyfluoropropenes such as $CF_3CH=CH_2$ (1243), $CF_3CF=CH_2$ (1234), $CF-CF=CHF$ (1225) or their isomers which are very difficult to separate from F134a by distillation because their boiling points are very close to that of 134a.

Many processes for the purification of F134a, and in particular for removing F1122 in F134a, have already been proposed. Mention may thus be made of:
- catalytic hydrogenation of F1122 and/or of other fluorinated olefins (WO 9008750, JP 02273634 or JP 04095037);
- adsorption of the impurities on active charcoal (EP 389334) or on molecular sieves (U.S. Pat. Nos. 4,906,796, JP 03072437, EP 503,796, EP 511,612 or EP 526,002);
- oxidation of F1122 by aqueous potassium permanganate (U.S. Pat. No. 4,129,603).

None of these processes is entirely satisfactory from the industrial viewpoint. Thus, the treatment with aqueous permanganate requires drying the F134a after the purification, which greatly increases the cost of this treatment. Physical adsorption on charcoal or molecular sieve can only be industrially envisaged for a finishing treatment because, taking into account the adsorption capacities of the proposed materials, it appears entirely uneconomical to treat products containing more than a few tens of ppm of adsorbable impurities. Moreover, according to the documents cited above, these adsorption techniques only make it possible to remove F1122 and not $C_3$ or $C_4$ olefins. Catalytic hydrogenation requires special plants (compatible with hydrogen) which can only be envisaged industrially if the F134a has itself already been obtained according to a hydrogenolysis process.

Other proposed processes, such as fluorination of the olefins with elemental fluorine (EP 548,744), are also all industrially unadvantageous.

A more advantageous technique is that described in U.S. Pat. No. 4,158,675, which relates to a process for the removal of F1122 consisting in reacting the gases resulting from the main reaction:

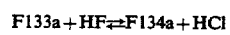

F133a+HF⇌F134a+HCl without separation of HCl, HF or unconverted F133a, in a second reactor maintained at a lower temperature than that of the main reaction. From a gas mixture whose F1122 content, relative to the organic compounds, is 5,300 vpm (volume per million), the in-line treatment at 160° C. leads to an F1122 value of 7 vpm.

In this process, the impurity removed (F1122) is refluorinated to F133a, that is to say to a recyclable product. However, the major disadvantage of this process lies in the necessity of having to treat a significant gas flow rate and thus resulting in a high reaction volume, which leads to a prohibitive investment and a prohibitive maintenance cost. Moreover, the process also only relates to the removal of F1122.

In order to avoid these disadvantages, it has been proposed to treat a gaseous mixture of crude F134a and HF in the gas phase, in the absence of hydrochloric acid, in the presence of a fluorination catalyst (JP 04321632, EP 548,742 and Application FR 9,209,700). During this treatment, hydrofluoric acid is added to F1122 and certain other (chloro)fluorinated olefins, such as $CF_2=CFH$ (F1123) or $CF_3CH=CHCF_3$ (F1336), and converts them to saturated compounds which are easier to separate and/or recycle by distillation. This process is particularly elegant but, unfortunately, it has been observed that, while F1122 is particularly easy to remove according to this method, other fluorinated olefins such as, for example, the fluoropropenes F1243, 1234 and 1225 have very little reactivity under these conditions and cannot be entirely removed according to this process.

DESCRIPTION OF THE INVENTION

In order to avoid the disadvantages of the abovementioned techniques, the present invention proposes a particularly efficient and economic means for purifying a crude F134a containing unsaturated impurities.

The process according to the invention consists in treating a gaseous mixture of crude F134a, CF and oxygen or air, in the gas phase, at a temperature between 200° and 350° C. and at a pressure ranging from atmospheric pressure to 2.5 MPa, in the presence of a fluorination catalyst, the HF/F134a molar ratio being between 0.05 and 0.5 and the $O_2$/F134a molar ratio being between 0.001 and 0.1.

In a crude F134a, the level of olefinic impurities can vary between 50 and 15,000 ppm (0.005 to 1.5%) with respect to F134a and is most often between 500 and 5,000 ppm (0.05 to 0.5%). Besides (chloro)fluorinated olefins, crude F134a can also contain variable quantities of other compounds such as, for example, F133a (0 to 7%), 1,1,1-trifluoroethane (F143a), monochlorotrifluoroethane (F124) and pentafluoroethane (F125); the presence of these saturated impurities does not harm the efficiency of the process according to the invention in any way.

Among (chloro)fluorinated olefinic impurities present in crude F134a, F1122 is generally the most important impurity. Other possible olefinic impurities such as F1123, F1243, F1234, F1225, F1318, F1327, F1326 and F1336 are either not present or are generally present at low contents (10 to 500 ppm); among the latter, the various F1243, F1234 and F1225 are the most troublesome.

By virtue of the joint use of HF and $O_2$, the process according to the invention makes it possible to significantly reduce the majority of (chloro)fluorinated olefins. It makes it possible to convert not only F1122 but also $C_3$ olefins (F1243, F1234, F1225, and the like) which are particularly difficult to remove by treatment with hydrofluoric acid alone.

In the process according to the invention, (chloro)-fluorinated olefins such as F1122, 1123, 1243, 1234, 1225, 1318, 1327, 1336 and the like can react either with HF or with oxygen. F1122, which is the main impurity, can thus be converted to F133a or its oxidation products (CO, $CO_2$, $COF_2$, and the like). The mechanism of reaction of these olefins with oxygen is not entirely known but it may be supposed that they react through the intermediate formation of an epoxide which can rearrange:

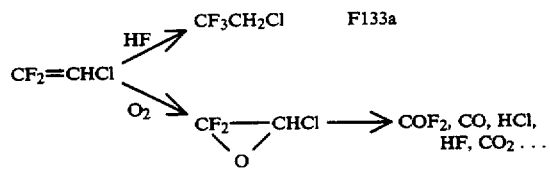

As F133a is directly recyclable to the fluorination reactor, it is very obviously of advantage to favor the first reaction. Taking account of the differences in reactivity with HF of F1122 and other olefins present in crude F134a, it could be shown that a good choice of the operating conditions makes it possible to minimize the side production of oxidation products of F1122 while virtually quantitatively converting both F1122 and the other olefins such as F1243, F1234 and F1225. Fluorination of F1122 to F133a thus makes it possible to convert this impurity to a product which is recyclable to the reactor but this predominance of fluorination over oxidation of F1122 does not limit the invention because, in the case of small quantities of F1122, the loss by oxidation is not significant.

During the implementation of the process according to the invention, oxygen (or air) can react with F134a or with certain saturated impurities such as F133a to provide oxidation and combustion products of these products (CO, $CO_2$, $COF_2$, and the like). Although these oxidation products are not troublesome and can be easily separated from F134a, it is nevertheless advantageous to minimize these side reactions because they are reflected by a loss in yield.

By a judicious choice of the operating conditions (temperature, contact time, $O_2$/F134a and HF/F134a molar ratios), it is possible to minimize these combustion reactions of F134a or of other saturated products possibly present in F134a and to react oxygen mainly with olefinic impurities. The choice of the temperature is particularly important for obtaining a selective reaction without significant side production of oxidation products of F134a or possibly of F133a. The choice of the HF/F134a molar ratio is also very important because, in the absence of HF, the removal of olefins is less efficient and less selective. Degradation of F134a by oxidation is, in this case, markedly more significant than in the presence of HF.

The catalytic treatment in the gas phase of crude F134a with HF and oxygen or air according to the invention is advantageously carried out at a temperature between 200° and 350° C., preferably between 225° and 300° C., and at a pressure between atmospheric pressure and 2.5 MPa, preferably between atmospheric pressure and 1.5 MPa.

The contact time can vary between 10 and 200 seconds but a contact time of between 20 and 100 seconds is preferred.

As mentioned above, the HF/F134a molar ratio can vary between 0.05 and 0.5. However, it is preferable to operate with an CF/F134a molar ratio of between 0.125 and 0.200 and, more particularly, a molar ratio close to that corresponding to the HF/F134a azeotrope (0.15).

The $O_2$/F134a molar ratio can vary between 0.001 and 0.1 but it is preferable to operate with an $O_2$/F134a molar ratio between 0.005 and 0.05.

At the conclusion of the treatment according to the invention, the gas flow no longer contains, or only contains traces of, olefinic impurities and can then be subjected to conventional operations (washing with water, washing with a sodium hydroxide/sodium sulphite solution, drying, distillation and the like) in order to separate unconverted HF, oxygen or air and saturated compounds other than F134a.

If it is desired to minimize phenomena of entrainment of F134a by inert gases such as nitrogen, it will generally be preferred to use pure oxygen rather than air. However, the latter may be preferred because it makes possible an easier implementation of the process.

The fluorination catalysts to be used for the implementation of the process according to the invention can be bulk catalysts or supported catalysts, the support which is stable in the reaction medium being, for example, an active charcoal, alumina, partially fluorinated alumina, aluminium fluoride or aluminium phosphate. In the case of charcoal, combustion of the support will be avoided by taking the usual precautions.

Among the bulk catalysts, there may be mentioned more particularly chromium oxide prepared according to any one of the methods known to those skilled in the art (sol/gel process, precipitation of the hydroxide from chromium salts, reduction of chromic anhydride, and the like). Derivatives of metals such as nickel, iron, manganese, cobalt or zinc may also be suitable, alone or in combination with chromium, in the form of bulk catalysts but also in the form of supported catalysts.

Supported catalysts can be used in the form of balls, extrudates, pellets or even, if the operation is carried out in a stationary bed, in the form of fragments. For bulk catalysts, the pellet or ball form is generally preferred. When the operation is carried out in a fluid bed, it is preferable to use a catalyst in the form of balls or extrudates.

As non-limiting examples of catalysts, there may be mentioned:

microbeads of chromium oxide obtained by the sol/-gel process as described in Patent FR 2,501,062, catalysts of chromium oxide deposited on active charcoal (U.S. Pat. No. 4,474,895), on aluminium phosphate (Patent EP 55,958) or on aluminium fluoride (U.S. Pat. Nos. 4,579,974 and 4,579,976), mixed catalysts of chromium oxide and nickel fluoride deposited on aluminium fluoride (Patent Application EP 0,486,333), bulk catalysts based on chromium and nickel oxides (Patent Application EP 0,546,883).

The abovementioned patents, the contents of which are incorporated here by reference, broadly describe the method of preparing these catalysts, but also their method of activation, that is to say of prior conversion of the catalyst to stable active species by fluorination using gaseous HF diluted by inert compounds (nitrogen) or non-inert compounds (air or 1,1,2-trichloro-1,2,2-trifluoroethane). During this activation, the metal oxides which serve as active material (for example chromium oxide) or as support (for example alumina) can be partially or completely converted to the corresponding fluorides.

EXAMPLES

The following examples illustrate the invention without limiting it. Except when otherwise indicated, the contents (% and ppm) indicated are expressed as volume.

EXAMPLE 1 (Comparative)

This example is intended to illustrate the reactivity of the olefins F1243, F1234 and F1225 with HF, without oxygen, in the presence of a fluorination catalyst.

100 ml of a catalyst based on nickel fluoride and chromium oxide deposited on aluminium fluoride were placed in a tubular reactor made of Inconel 600 with an internal diameter of 28 nun and a volume of 200 ml. The physicochemical characteristics of this catalyst, prepared as described in Patent Application EP 0,486,333 and activated in a stationary bed by a nitrogen/HF mixture, are the following:

Chemical composition (by weight)

fluorine: 58.6%
aluminium: 25.9%
nickel: 6.4%
chromium: 6.0%
oxygen: 3.1%

Physical properties apparent density (in bulk): 0.85 g/ml
BET surface: 23 m²/g
volume of the pores with a radius between 4 nm and 63 μm: 0.4 ml/g
surface of the pores with a radius greater than 4 nm: 23 m²/g After a final "in situ" activation of the catalyst using an HF/F133a (molar ratio: 0.4) gas mixture between 25° and 250° C., the reactor was fed with a gas mixture consisting of HF and crude F134a in proportions such that the HF/F134a molar ratio is equal to 0.2, that is to say close to the azeotropic composition.

The F134a used contained 50 ppm of F1243+F1234 and 14 ppm of F1225. F1243 and F1234 were not separated under the analysis conditions (gas phase chromatography) and the 50 ppm correspond to the F1243+F1234 sum. Other analyses of the same mixture have nevertheless shown that the F1243 content was greater than that of F1234.

The absolute pressure of the reactor was fixed at 1.2 MPa and the feed flow rate (f) of the F134a+HF mixture was adjusted so as to have a contact time (t) of 80 seconds, f and t being linked by the relationship:

$$t = \frac{3600 \times V \times 273 \times P \times 10}{22.4 \times f \times (T + 273)}$$

where P = pressure in MPa
t = contact time in seconds
f = flow rate in mol/hour
V = bulk catalyst volume, expressed in litres
T = temperature of the reactor in degrees Celsius.

A gas sample, freed of excess HF, was analyzed by GPC at the reactor outlet in order to monitor the development in the level of olefins in the organic products.

Two tests were carried out respectively at 250° and 300° C.(duration 48 hours) and the following results were obtained:

| Level of olefins at the reactor outlet (in ppm) | | |
| --- | --- | --- |
| | 250° C. | 300° C. |
| F1243 + F1234: | 30 | 20 |
| F1225: | 12 | 12 |

A mixture of HF and F134a (HF/F134a molar ratio: 0.18) was then passed into the same reactor, over the same catalyst, under the same pressure and contact time conditions; the F134a contained 2,400 ppm of F1122. As above, two tests were carried out at 250° C. and 300° C. and, in both cases, the residual F1122 content was less than 5 ppm.

These tests thus very clearly show that the olefins F1234, F1243 and especially F1225 are markedly less reactive with respect to HF than F1122 and that it is virtually impossible to remove them entirely.

EXAMPLE 2 (Comparative)

This example, carried out at atmospheric pressure with a catalyst analogous to that of Comparative Example 1, is intended to illustrate the poor selectivity of the oxidation reaction in the absence of HF.

300 ml of a catalyst having the following composition by weight were placed in a reactor made of Inconel 600 with an internal diameter of 40 mm:

fluorine: 56.0%
aluminium: 24.0%
nickel: 6.5%
chromium: 6.0%
oxygen: 7.5%

After activation of the catalyst with an HF/N₂ mixture and then with pure HF at 360° C. for one hour, an oxidation test of a F134a in the absence of HF was carried out under the following conditions:

Temperature: 275° C.
Pressure: atmospheric
$O_2$/F134a molar ratio: 0.01
Contact time: 80 seconds The F134a used contained 40 ppm of F1243+F1234 and 4 ppm of F1225.

After operating for 25 hours under these conditions, analysis of the gases, after washing with water in a gas washing bottle, gave the following results:

F1243+F1234: 13 ppm
F1225: 9 ppm
F1123 ($CF_2$=CFH) formed: 14 ppm
CO formed: 1%
$CO_2$ formed: 0.45%

These results clearly show the great sensitivity of F134a to oxidation in the absence of HF since the high CO and $CO_2$ contents can only arise from the oxidation of F134a. They also show that, in the absence of HF, removal of olefins is very difficult and that there was even formation of F1225 and F1123.

EXAMPLE 3

An HF/F134a/$O_2$ mixture was passed into the same reactor and with the same catalyst as in Comparative Example 2 under the following conditions:
Pressure: atmospheric
Contact time: 79 to 83 seconds
HF/F134a molar ratio: 0.2 to 0.5
$O_2$/F134a molar ratio: 0.002 to 0.03
Temperature: 275° C.
The F134a contained 40 ppm of F1243+F1234 and 4 ppm of F1225.
The following results were obtained:

| MOLAR RATIO | | RESIDUAL OLEFIN LEVELS (ppm) | | CO | $CO_2$ |
|---|---|---|---|---|---|
| $O_2$/F134a | HF/F134a | F1243 + F1234 | F1225 | (%) | (%) |
| 0.002 | 0.25 | 18 | <1 | N.A.* | N.A.* |
| 0.005 | 0.30 | 8 | 3 | 0.09 | <0.1 |
| 0.01 | 0.50 | 9 | 3 | <0.1 | <0.1 |
| 0.01 | 0.52 | <1 | <1 | 0.2 | 0.15 |
| 0.03 | 0.30 | 7 | 4 | 0.1 | <0.1 |

Compared with Example 2, these results clearly illustrate that, in the presence of HF, removal of $C_3$ olefins is more efficient but also more selective.

The increase in the HF/F134a molar ratio is reflected in a decrease in the formation of CO and $CO_2$ arising essentially from the oxidation of F134a.

EXAMPLE 4

An F134a/HF/air mixture was passed into the same reactor and with the same catalyst as in Comparative Example 1 under the following conditions:
Pressure: 0.8 MPa
Contact time: 87 seconds
HF/F134a molar ratio: 0.2
Air/F134a molar ratio: 0.1
Temperature: 275° C.
The F134a used contained, inter alia, the following impurities:
F133a: 5%
F124: 0.8%
F1122: 2700 ppm
F1243+F1234: 35 ppm
F1225: 11 ppm
At the reactor outlet, the olefin contents were the following:
F1122: 2 ppm
F1243+F1234: 8 ppm
F1225: 4 ppm

EXAMPLE 5

An HF/F134a/$O_2$ mixture was passed into the same reactor and with the same catalyst as in Comparative Example 1 under the following conditions:
Pressure: 1.2 MPa
Contact time: 80 or 180 seconds
HF/F134a molar ratio: 0.2
$O_2$/F134a molar ratio: 0.002 to 0.01
Temperature: 250° to 300° C.
The F134a contained 50 ppm of F1243+F1234 and 14 ppm of F1225.
The following results were obtained:

| Temperature (°C.) | $O_2$/F134a molar ratio | Residual olefin levels (ppm) | | Degree of oxidation of F134a | |
|---|---|---|---|---|---|
| | | F1243 + F1234 | F1225 | CO (%) | $CO_2$ (%) |
| 300 | 0.01 | 8 | 4 | 1 | 1 |
| 275 | 0.01 | 4 | 2 | 1 | 1 |
| 250 | 0.01 | 25 | 10 | 0.1 | 0.1 |
| 275 | 0.005 | 13 | 5 | 0.5 | 0.5 |
| 275 | 0.002 | 18 | 10 | 0.1 | 0.1 |
| 275* | 0.005 | 12 | 10 | 0.3 | 0.3 |

*Test carried out with a contact time of 180 seconds in place of 80 seconds for the others.

The results of these tests show that the simultaneous action of HF and oxygen makes it possible to remove the olefins F1243, F1234 and F1225 to very low values. The temperature of 275° C. constitutes an optimum.

EXAMPLE 6

50 ml of a catalyst consisting of microbeads of bulk chromium oxide, prepared as described in Example 3 of Patent FR 2,501,062, were placed in a tubular reactor made of Inconel 600 with an internal diameter of 28 mm and a volume of 200 ml. This catalytic reactor, operating as a stationary bed, was then fed with a mixture, in the gas state, consisting of crude F134a, HF and oxygen in proportions such that the HF/F134a molar ratio is equal to 0.20 and that the F134a molar ratio is equal to 0.01.

The crude F134a contained, inter alia, the following impurities:
F124: 2%
F133a: 3.4%
F1122: 1370 ppm
F1243+F1234: 173 ppm
F1225: 457 ppm The temperature of the reactor was fixed at 275° C. and the feed flow rate of the mixture was adjusted so as to have a contact time of 80 seconds at a pressure of 1.2 MPa.

Analysis of the product. exiting from the reactor, after removal of excess HF, provided the following results:
F1122: 6 ppm
F1243+F1234: 35 ppm
F1225: 12 ppm

We claim:
1. Process for the purification of a crude 1,1,1,2-tetrafluoroethane (F134a) containing unsaturated impurities, comprising treating a gaseous mixture of crude 1,1,1,2-tetrafluoroethane,, hydrofluoric acid and oxygen or air in the gas phase, at a temperature between 200° and 350° C. and at a pressure ranging from atmospheric pressure to 2.5 MPa, in the presence of a fluorination catalyst, the HF/F134a molar ratio being between 0.05 and 0.5 and the $O_2$/F134a molar ratio being between 0.001 and 0.1.

2. Process according to claim 1, wherein the unsaturated impurities are 1-chloro-2,2-difluoroethylene and/or $C_3$ or $C_4$ (chloro)fluorinated olefins.

3. Process according to claim 1 wherein the reaction is carried out at a pressure between atmospheric pressure and 1.5 MPa.

4. Process according to claim 1, wherein the contact time is between 10 and 200 seconds.

5. Process according t claim 1, wherein the HF/F134a molar ratio is between 0.125 and 0.200.

6. Process according to claim 1, wherein the $O_2$/F134a molar ratio is between 0.005 and 0.05.

7. Process according to claim 1, wherein the reaction is carried out with pure oxygen.

8. Process according to claim 1, wherein air is used.

9. Process according to claim 1, wherein the fluorination catalyst is a bulk or supported catalyst based on chromium, nickel, iron, manganese, cobalt and/or zinc.

10. Process according to claim 4, wherein the contact time is between 20 and 100 seconds.

* * * * *